United States Patent
Welsch et al.

(10) Patent No.: US 9,856,391 B2
(45) Date of Patent: Jan. 2, 2018

(54) PROCESS FOR PRODUCTION OF HIGH SOLIDS STARCH DISPERSION USING MULTI-STAGE DEGRADATION

(71) Applicant: TRINSEO EUROPE GmbH, Horgen (CH)

(72) Inventors: Gregory W. Welsch, Midland, MI (US); Giona Kilcher, Zurich (CH); Pekka Johannes Salminen, Freienbach (CH); David L. Church, Midland, MI (US); Dustin E. Burton, Sanford, MI (US); David E. Hammond, Saginaw, MI (US)

(73) Assignee: TRINSEO EUROPE GMBH, Horgen (CH)

( * ) Notice: Subject to any disclaimer, the term of this patent is extended or adjusted under 35 U.S.C. 154(b) by 27 days.

(21) Appl. No.: 14/782,659

(22) PCT Filed: Apr. 10, 2014

(86) PCT No.: PCT/EP2014/057257
§ 371 (c)(1),
(2) Date: Oct. 6, 2015

(87) PCT Pub. No.: WO2014/167051
PCT Pub. Date: Oct. 16, 2014

(65) Prior Publication Data
US 2016/0046819 A1    Feb. 18, 2016

Related U.S. Application Data

(60) Provisional application No. 61/810,504, filed on Apr. 10, 2013.

(51) Int. Cl.
| | | |
|---|---|---|
| *C09D 103/00* | (2006.01) | |
| *C09D 103/02* | (2006.01) | |
| *C08B 30/08* | (2006.01) | |
| *C08B 30/12* | (2006.01) | |
| *C08B 30/14* | (2006.01) | |
| *C09J 103/02* | (2006.01) | |
| *D21H 19/54* | (2006.01) | |
| *C12P 19/14* | (2006.01) | |
| *C09D 101/02* | (2006.01) | |
| *C09D 109/06* | (2006.01) | |
| *C09D 133/00* | (2006.01) | |

(52) U.S. Cl.
CPC ............ *C09D 103/02* (2013.01); *C08B 30/08* (2013.01); *C08B 30/12* (2013.01); *C08B 30/14* (2013.01); *C09D 101/02* (2013.01); *C09D 109/06* (2013.01); *C09D 133/00* (2013.01); *C09J 103/02* (2013.01); *C12P 19/14* (2013.01); *D21H 19/54* (2013.01)

(58) Field of Classification Search
CPC ..................................................... C09D 103/02
See application file for complete search history.

(56) References Cited

U.S. PATENT DOCUMENTS

| | | | | |
|---|---|---|---|---|
| 6,737,099 | B2 * | 5/2004 | Guraya | ................ A23G 3/346 426/622 |
| 2006/0078485 | A1 | 4/2006 | Thiele et al. | |
| 2011/0300394 | A1 * | 12/2011 | Welsch | ................ C08B 30/02 428/532 |

FOREIGN PATENT DOCUMENTS

| | | |
|---|---|---|
| WO | WO 2005/095277 A1 | 10/2005 |
| WO | WO 2013/032673 A1 | 3/2013 |

OTHER PUBLICATIONS

Uthumporn et al, Hydrolysis of granular starch at sub-gelatinization temperature using a mixture of amylolytic enzymes, 2010, food and bioproducts processing, vol. 88, issue 1, pp. 47-54.*
Durand, G.A., et al., "Dynamic optimization of the mashing process," *Food Control*, 20(12):1127-1140 (2009).
International Preliminary Report on Patentability for International Application No. PCT/EP2014/057257, dated Oct. 22, 2015 (6 pages).
International Search Report and Written Opinion for International Application No. PCT/EP2014/057257, dated May 26, 2014 (9 pages).
Uthumporn, U., et al., "Hydrolysis of granular starch at sub-gelatinization temperature using a mixture of amylolytic enzymes," *Food and Bioproducts Processing*, 88(1):47-54 (2010).

* cited by examiner

*Primary Examiner* — Melvin C Mayes
*Assistant Examiner* — Stefanie Cohen
(74) *Attorney, Agent, or Firm* — Eric D. Babych; Brinks Gilson & Lione

(57) ABSTRACT

A process for preparing a starch dispersion may include combining a feed starch and an aqueous liquid to form a starch slurry. The starch slurry may be subjected to a first degradation treatment to form a first mixture. A temperature of the starch slurry during the first degradation treatment may be less than a gelation temperature. The first mixture may be heated to a temperature between the gelation temperature and a solubilization temperature. The heated first mixture may be subjected to a second degradation treatment to form a second mixture. The second mixture may be sheared to form the starch dispersion.

10 Claims, No Drawings

PROCESS FOR PRODUCTION OF HIGH SOLIDS STARCH DISPERSION USING MULTI-STAGE DEGRADATION

FIELD OF DISCLOSURE

Embodiments of the present disclosure are directed toward a process for preparing starch dispersions. More specifically, embodiments are directed toward a process for multiple stage chemically assisted mechanical degradation of starch to form stable dispersions of starch particles.

BACKGROUND

Synthetic latexes are important components in the binder systems of coatings used in the paper coating industry. Synthetic latexes used in these applications typically have a high solids content (e.g., 48-58 weight percent solids) and a low viscosity that allows for ease of handling, and good runnability and stability in the paper coating process. Synthetic latexes also allow for excellent particle size control, viscoelasticity control (e.g., glass transition temperature (Tg) and modulus), and dry and wet strength of the resulting coatings.

In addition to synthetic latexes, starch can be useful in the binder systems of coatings used in the paper coating industry. For example, starch has been used as a partial substitute for synthetic latexes in the binder systems of coatings used in the paper coating industry. Among its advantages, starch is a relatively low cost material having excellent water holding and thickening properties while providing stiffness, porosity, and blocking resistance to the resulting coating. There are, however, limitations in the use of starch in these applications. These limitations include, for example, poor runnability during application and poor product performance of the coating compositions, especially as the level of latex substitution increases.

To overcome these challenges, it would be advantageous to develop a starch product which can be stored at a high solid content (e.g., at least about 40 weight percent) while maintaining a low viscosity (e.g., 2000 cP or less), similar to synthetic latexes, and preferably with an average particle size diameter of no larger than 2 micrometers.

SUMMARY

A process for preparing a starch dispersion may include combining a feed starch and an aqueous liquid to form a starch slurry. The starch slurry may be subjected to a first degradation treatment to form a first mixture. A temperature of the starch slurry during the first degradation treatment may be less than a gelation temperature. The first mixture may be heated to a temperature between the gelation temperature arid a solubilization temperature. The heated first mixture may be subjected to a second degradation treatment to form a second mixture. The second mixture may be sheared to form the starch dispersion.

Definitions

As used herein, the terms "a," "an," "the," "one or more," and "at least one" are used interchangeably and include plural referents unless the context clearly dictates otherwise.

Unless defined otherwise, all scientific and technical terms are understood to have the same meaning as commonly used in the art to which they pertain. For the purpose of the present disclosure, additional specific terms arc defined throughout.

As used herein, "μm" is an abbreviation for micrometer.

As used herein, "° C." is an abbreviation for degree Celsius.

As used herein, "cP" is an abbreviation for Centipoise, a unit f measurement in the cgs system for viscosity.

The terms "comprises," "includes" and variations of these words do not have a limiting meaning where these terms appear in the description and claims. Thus, for example, a process that comprises "a" feed starch can be interpreted to mean a process that includes "one or more" feed starches. In addition, the term "comprising," which is synonymous with "including" or "containing," is inclusive, open-ended, and does not exclude additional unrecited elements or method steps.

As used herein, the term "and/or" means one, more than one, or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "feed starch" can include, a carbohydrate polymer composed of various ratios of amylose and amylopectin joined by glucosidic bonds and being in a crystalline or semi-crystalline state. The feed starch can be selected from a wide variety of sources including, but not limited to, corn, potato, tapioca, rice, wheat, barley, and other grains and/or tubers (e.g., root or stem tubers), and of those may include waxy, native, unmodified native, and/or high amylose starches. Specific non-limiting examples include waxy corn starch (e.g., a high amylopectin starch) and dent starch, among others. The feed starch can also include "modified" feed starch which can include a modified starch (e.g., corn, potato, tapioca, among others) prepared by acetylation, chlorination, acid hydrolysis, enzymatic action, or other modification process. This "modified" feed starch can be purposefully modified to deliver other benefits such as carboxylated starches, hydroxyethylated starches, resistant starches, thermally oxidized starches, dextrin type, among others. In one or more embodiments, the feed starch can have a number of different properties and/or forms. These may include, but are not limited to, a dry powder and/or an intermediate starch product such as a cake, and/or a slurry having moisture content in the range of less than or equal to 80 weight percent, for example, in the range of from 35 to 80 weight percent; or in the alternative from 35 to 75 weight percent; or in the alternative from 35 to 65 weight percent. In one or more embodiments, the feed starch has discrete units having an average particle size diameter of about 15 to about 40 micrometer (μm); for example, from 15 to 35 μm; or in the alternative, from 15 to 30 μm; or in the alternative from 20 to 40 μm. Mixtures of two or more of the feed starches provided herein are also possible, and would be considered to be a "feed starch" as provided and discussed herein.

As used herein, the term "dry" means no greater than about 8 to about 14 percent water by weight absorbed in and/or bound to a substance (e.g., the feed starch).

As used herein, the term "cross-linker" means a compound that attaches at least two chains of polymer molecules through covalent or hydrogen bonds. Different categories of a cross-linker may include, but are not limited to, Amino Resins (Urea Formaldehyde and Melamine Formaldehyde), Glyoxal Resins, and Metallic Ions (Zirconium complexes). If a cross-linker is employed with the dispersion of the present disclosure, the selection of the crass-linker can depend at least in part on the reactive groups available on the starch particles, the ingredients of the coating, binder and/or adhesive composition, and/or the end use of the coated substrate. The term insolubilizer also is often used to define the function of crosslinking chemistry in conjunction with starch.

As used herein, the term "surfactant" means a compound that reduces surface tension when dissolved in water or water solutions, or that reduces interfacial tension between two liquids, or between a liquid and a solid.

As used herein, the term "soluble starch" means a starch released and/or leached from the feed starch granule into the aqueous liquid while being heated to or at a temperature ranging from a gelation temperature to below a solubilization temperature of the feed starch, where the soluble starch is present in the aqueous phase between the starch particles of the present disclosure. In one embodiment, the soluble starch may be characterized by being small enough so as not to scatter light in the visible spectrum (e.g., from about 380 or 400 nanometers to about 760 or 780 nanometers).

As used herein, the term "dispersion" means a two-phase system including particles dispersed in a continuous phase. The dispersion may include swollen starch particles or globules dispersed in an aqueous liquid, which forms the continuous phase as described herein. The starch particles can have an average particle size diameter of no larger than 2 micrometers.

As used herein, the term "starch particles" refers to discrete units derived from the feed starch using the methodology of the present disclosure, where the discrete units have an amorphous structure. The starch particles can have an average particle size diameter of no larger than 2 micrometers.

As used herein, the term "stable" or "stability" means the ability and the duration of the starch particles of the present disclosure to remain as a dispersion in the aqueous liquid (e.g., due to Brownian movement of the starch particles in the aqueous liquid), where any settling of the starch particles can be reversed by agitation. The stable dispersion of the starch particles of the present disclosure does not gel or "set-up" under the conditions of the dispersion given herein.

As used herein, the term "high shear mixer" refers to a high-shear mixing apparatus that disperses, or transports, the starch particles into the aqueous liquid, as provided herein, by mechanical agitation. The high shear mixer can be a rotor stator mixer. The rotor stator mixer includes at least one impeller or rotor, or a series of impellers and/or rotors, powered by a motor (e.g. an electric motor) and at least one stationary component (e.g., a stator) that creates a close clearance gap with the rotor so as to produce an extremely high shear zone for the material (e.g., the feed starch) as it exits the rotor. Factors such as the diameter of the rotor and its rotational speed (e.g. ramps and cycles), the design of the stator ring such as number, size, and rows of teeth and their angle, the distance between the rotor and the stator (e.g., the clearance gap), the residence time, and the number of rotor stator mixers used all can affect the generation of the dispersion of the starch particles in the aqueous liquid. Examples of such high-shear mixing apparatus include, but are not limited to, batch high shear mixers, inline high shear mixers, ultra high shear inline mixers, and grinding mills. In one embodiment, the term "high shear mixer" excludes an extruder, As used herein, the term "gelation temperature" refers to a temperature at which the crystalline structure of the feed starch transforms at least partially from its crystalline and/or semi-crystalline state to combine with the aqueous liquid to produce a viscous jelly-like product. The gelation temperare may vary with pressure and/or the type of starch employed in the dispersion.

As used herein, the term "solubilization temperature" refers to a temperature at which the feed starch has substantially no remaining crystallinity and becomes a substantially uniformly dispersed mixture at the molecular level in and with the aqueous liquid. The solubilization temperature may vary with pressure and/or the type of starch employed in the dispersion.

As used herein, the terms "swell," "swelling," and/or "swollen," refer to an increase in the volume of the feed starch due, at least in part, to a loss in crystallinity of the initial structure of the feed starch and the absorption of an aqueous liquid into the resulting amorphous structure of the feed starch.

As used herein, the term "ambient conditions" refers to a temperature of around 25° C. (e.g., 25° C.) and a pressure of around 101.325 kiloPascal (kPa) (e.g., 1 atmosphere).

As used herein, the term "specific mechanical energy (SME)" is defined as the total input of mechanical energy per unit mass of material flowing through the high shear mixer. The units of SME presented herein are in Joules per gram (J/g).

As used herein, the term "redispersible" is defined as a powder formulation that readily disperses and hydrates into an aqueous liquid. The polymer powders are typically produced by subjecting an aqueous dispersion of the polymer to a drying operation in which its volatile components are evaporated (e.g., by spray drying or freeze drying). The evaporation of the aqueous dispersion medium may be accompanied by irreversible aggregation of the polymer particles of the aqueous dispersion with one another to form secondary particles. The formation of secondary particles results in worse redispersibility, which is generally accompanied by worse performance properties of the powder. Therefore, good redispersibility in liquid is one of the most important properties of the redispersible polymer powders.

DETAILED DESCRIPTION

Embodiments of the present disclosure describe the use of a high shear mixer for producing a dispersion of starch particles in an aqueous liquid. The starch particles are formed from a feed starch. Subjecting the feed starch/ aqueous liquid mixture to multiple degradation treatments at predetermined points during the process aids in production of the dispersion as described herein. The degradation treatments may be configured to degrade (e.g., reduce or cleave) soluble starch present in the aqueous phase during the process as further described herein. The feed starch is combined with the aqueous liquid. The combined feed starch and aqueous liquid is subjected to a first degradation treatment to form a first mixture. A first temperature of the feed starch/aqueous liquid mixture during the first degradation treatment is less than a gelation temperature of the feed starch. The first mixture is heated to a second temperature that is between the gelation temperature and a solubilization temperature of the feed starch. At the second temperature, the structure of the feed starch may swell as it at least partially loses its crystalline structure and absorbs at least a portion of the aqueous liquid to form an amorphous structure.

Thereafter, the heated first mixture is subjected to a second degradation treatment to form a second mixture. The feed starch (e.g., the feed starch present in the second mixture) is sheared to form the starch particles of the dispersion. The feed starch may be swollen during shearing, which may enhance the effectiveness of the shearing process. The dispersion may have improved shelf-stability, high solids content, and low viscosity, as further described herein. The multi-stage degradation (e.g., the multiple degradation treatments at predetermined points during the process) may enable the viscosity of the feed starch/aqueous liquid mixture to be controlled throughout the process. As a result, starch dispersions may be produced using a variety of different feed starches such as, for example, a waxy starch (e.g., waxy corn starch), a native dent starch (e.g., dent corn starch), any other corn starch, a potato starch, a tapioca starch, a rice starch, a wheat, barley starch, a starch derived from any other grain and/or tuber, and combinations thereof as further described herein. Additionally, or alternatively, the feed starch may include waxy starch, native starch, unmodified native starch, high amylose starch, or combinations thereof.

Maintaining the feed starch below the solubilization temperature throughout the process may prevent overheating and/or cooking of the starch. For example, processing the feed starch as described herein may gelatinize the feed starch without cooking the feed starch. The gelatinized feed starch may be swollen and/or hydrated as described herein, without losing its amorphous structure to an undesirable extend (e.g., without being solubilized to an undesirable extent). The gelatinized feed starch may be torn into discrete particles (e.g., by shearing) to form the dispersion. The starch particles of the dispersion may have an amorphous structure similar to that of the swollen feed starch. This may enable the dispersion of the starch particles in the aqueous medium to have enhanced shelf-stability as described herein. This is distinguishable from a process in which the feed starch is heated to the solubilization temperature (e.g., an extrusion or a jet-cooking process). Upon reaching the solubilization temperature, the feed starch would at least partially lose its amorphous structure such that starch particles having the desired structure and/or size could not be formed in the manner described herein.

The gelatinization of a high solids starch slurry generally results in a solution that exceeds the processing window of a typical rotor stator mixer. It may be difficult or even impossible to homogeneously mix such a solution in the rotor stator mixer. Poor mixing (e.g., non-homogeneous mixing) may result in localized overheating of the starch and/or cooking of the starch, which may be undesirable when gelation without cooking is intended. Multiple degradation treatments at predetermined points during the processing of the starch, as described herein, may aid in controlling the viscosity of the mixture to enable relatively homogeneous mixing. Although the process is generally described herein as including two degradation treatments, this disclosure is not so limited. The process may include any number of multiple degradation treatments (e.g., two, three, or more degradation treatments) at predetermined points during the process. Additionally, or alternatively, the multiple degradation treatments may be consecutive with one another (e.g., without substantial delay between degradation treatments). For example, the multiple degradation treatments may be configured as a substantially continuous addition of a degradation agent throughout one or more predetermined stages of the process. Additionally, or alternatively, each degradation treatment (e.g., the first degradation treatment and/or the second degradation treatment) may include a single degradation treatment or a plurality of degradation treatments. For example, the first degradation treatment and/or the second degradation treatment may include two or more discrete degradation treatments. The multiple degradation treatments may enable the viscosity of the mixture and/or gelation of the starch to be controlled to maintain processing efficiency.

In one embodiment, the process for preparing the starch dispersion includes combining the feed starch and the aqueous liquid. Throughout this disclosure, the term "feed starch/aqueous liquid mixture" may refer to the mixture at any stage throughout the process. For example, the feed starch/aqueous liquid mixture may refer to a starch slurry, a first mixture, a second mixture, or any other mixture including the feed starch and the aqueous liquid (with or without additional components) as described herein. The combined feed starch and aqueous liquid may form a starch slurry. For example, the feed starch and the aqueous liquid may be combined in a vessel (e.g., a tank or a pipe) to form the starch slurry. The vessel may be a component of the high shear mixer (e g., a bowl or a tank of a rotor stator mixer). Additionally, or alternatively, the starch slurry may be fed from the vessel to the high shear mixer (e.g., an inline high shear mixer or a batch high shear mixer). The feed starch and the aqueous liquid may be mixed (e.g., by the high shear mixer or another mixer) during combination of the feed starch and the aqueous liquid to disperse the teed starch in the aqueous liquid. Such mixing may increase the temperature of the starch slurry as further described herein. Additionally, or alternatively, heat may be supplied and/or removed from the starch slurry during mixing as further described herein. The feed starch may be combined with the aqueous liquid as supplied by the manufacturer (e.g., as a dry powder, a cake, and/or a slurry). Additionally, or alternatively, the feed starch may be pre-wetted prior to combination with the aqueous liquid. The amount of aqueous liquid included in the starch slurry may include the amount of water in the feed starch (e.g., the moisture content of the feed starch). Additionally, or alternatively, the weight of water in the feed starch may be excluded from the calculation of the dry weight of the feed starch.

The temperature of the feed starch/aqueous liquid mixture may be controlled and/or adjusted during the process. For example, the vessel (e.g., of the high shear mixer) may include a temperature control device (e.g., a heating/cooling jacket or an inserted baffle) that may be used to control and/or adjust the temperature of the mixture. The temperature may include a mixing zone temperature measured at the mixing zone of the high shear mixer (e.g., near the interface of the rotor and the stator, or the discharge, of the rotor stator mixer) and/or a bulk temperature measured in a portion of the mixture away from the mixing zone of the high shear mixer. In one embodiment, heating and/or cooling may be provided by steam and/or water having a sufficient temperature difference with the feed starch/aqueous liquid mixture to cause heat transfer to and/or from the mixture. Additionally, or alternatively, the mixing and/or shearing action of the high shear mixer may add heat energy to the feed starch/aqueous liquid mixture. The added heat energy, or a portion thereof, may be removed by the temperature control device.

The initial temperature of the starch slurry may be less than the gelation temperature of the feed starch. Heat may be supplied to the starch slurry to increase the temperature of the starch slurry to a first temperature that is below the gelation temperature. Heat may be supplied by mixing and/or shearing the starch slurry, by the temperature control device, and/or by any other suitable method. The first temperature may be between about 5° C. and about 25° C. below the gelation temperature or between about 10° C. and about 20° C. below the gelation temperature. Upon heating to the first temperature, the viscosity of the starch slurry may tend to increase. The viscosity of the starch slurry may increase at a greater rate and/or to a greater extent depending on the type of starch that is used as the feed starch. Without wishing to be bound by any theory, it is believed that this increase in viscosity may be due to relatively low molecular weight starch chains leaching from the feed starch into the aqueous liquid during heating, swelling, and/or shearing of the feed starch as the starch slurry is mixed and/or heated. For example, at a temperature above about 63° C. under atmospheric conditions, amylose chains (if present) may leach out of the feed starch, which may create an unstable, high viscosity thickening effect in the starch slurry.

Soluble starch may be produced and/or released (e.g., into the aqueous phase) during the heating and/or shearing of the feed starch. The presence of the soluble starch may cause the viscosity of the starch slurry to increase. If the viscosity of the starch slurry is not controlled, the starch slurry may undesirably thicken to inhibit flow of the starch slurry within the vessel and/or through the high shear mixer as described herein. To aid in controlling the viscosity of the starch slurry, the soluble starch may be degraded (e.g., reduced or cleaved). For example, the soluble starch may be degraded by subjecting the starch slurry to a degradation treatment as described herein. Such degradation may reduce the molecular weight of the soluble starch from a first molecular weight to a second molecular weight that is less than the first molecular weight. Degrading the soluble starch may aid in reducing the viscosity of the starch slurry by reducing or cleaving the soluble starch into smaller fragments. The degradation treatment may degrade the soluble starch by any suitable method. For example, the degradation treatment may include addition of a degradation agent, thermal degradation, mechanical degradation, or combinations thereof to degrade the soluble starch.

The degradation agent may include any substance capable of degrading (e.g., reducing or cleaving) the soluble starch. To that end, the degradation agent may include, for example, an acid (e.g., hydrochloric acid, sulfuric acid, acetic acid, or citric acid), a base (e.g., sodium hydroxide, potassium hydroxide, or calcium hydroxide), an oxidizing agent (e.g., a persulfate such as ammonium persulfate or sodium persulfate, oxygen, ozone, hydrogen peroxide, peracetic acid, sodium chlorite, sodium hypochlorite, or a permanganate such as potassium permanganate), an enzyme (e.g., a glycoside hydrolase and/or an amylase such as an a-amylase), a microorganism (e.g., bacteria, fungi, archaea, algae, and/or protests), or combinations thereof. The degradation treatment may degrade the starch by any suitable method including, for example, chemical modification (e.g., acid or alkali hydrolysis), acid reduction, oxidative reduction, enzymatic reduction, microorganism action, physical and/or mechanical degradation (e.g., via the thermomechanical energy input of the processing equipment), or combinations thereof.

Thermal degradation may include applying thermal energy to (e.g., to adjust the temperature of) at least a portion of the soluble starch to cause the soluble starch to be at least partially degraded. Mechanical degradation may include applying mechanical energy to at least a portion of the soluble starch to cause the soluble starch to be at least partially degraded. In one embodiment, steam may be introduced into the feed starch/aqueous liquid mixture via a pressurized jet or nozzle. In this manner, thermal energy and mechanical energy may be applied to the soluble starch present in the mixture. The degradation of soluble starch caused by introduction of steam into the mixture may be one example of thermal and/or mechanical (e.g., thermomechanical) degradation of the soluble starch. Thermal and/or mechanical energy may be applied such that the temperature of the feed starch/aqueous liquid mixture remains at a desired level (e.g., below the gelation temperature or between the gelation temperature and the solubilization temperature) as described herein. In this manner, thermal degradation and/or mechanical degradation may be used to control the viscosity of the mixture without overheating and/or cooking the feed starch as described herein.

The feed starch/aqueous liquid mixture (e.g., the starch slurry) is subjected to a first degradation treatment to form a first mixture. The timing of the first degradation treatment may be just prior to the first sign of gelation or thickening of the continuous phase of the feed starch/aqueous liquid mixture. This may depend on the type of starch and/or the process conditions. The timing of the first degradation treatment may be critical to producing the desired effects as described herein. To that end, the feed starch/aqueous liquid mixture is subjected to the first degradation treatment while the mixture is at a temperature that is below the gelation temperature. For example, the mixture may be subjected to the first degradation treatment when the mixture reaches the first temperature and/or up to the onset of gelation as described herein. This may allow sufficient time for the degradation treatment to begin to reduce the soluble starch present in the feed starch/aqueous liquid mixture before reaching the gelation temperature. In this manner, the feed starch/aqueous liquid mixture may remain and/or be maintained below the gelation temperature during the first degradation treatment.

In one embodiment, the first degradation treatment may include addition of a first quantity of the degradation agent. The first quantity of the degradation agent may be added to the feed starch/aqueous liquid mixture (e.g., the starch slurry) to form the first mixture. The first quantity of the degradation agent may be added while the mixture is at a temperature that is below the gelation temperature (e.g., when the mixture reaches the first temperature and/or prior to the onset of gelation). This may allow sufficient time for the degradation agent to be thoroughly mixed into the feed starch/aqueous liquid mixture before reaching the gelation temperature. In this manner, the feed starch/aqueous liquid mixture may remain and/or be maintained below the gelation temperature during addition of the first quantity of the degradation agent to form the first mixture. Selection of the degradation agent may depend on the composition of the feed starch. The amount of the first quantity of the degradation agent added may depend on, for example, the type of degradation agent, the type of feed starch, the solids content, and/or the processing conditions. The concentration of the degradation agent in the dispersion produced as described herein (e.g., due to the addition of a first quantity and/or a second quantity of the degradation agent) may be, for example, between about 0.0001 weight percent and about 0.01 weight percent (e.g., between about 0.0001 weight percent and about 0.005 weight percent or between about 0.001 weight percent and about 0.01 weight percent) based the total weight of the dispersion.

In one embodiment, the degradation agent may include an acid. The soluble starch may be degraded by acid hydrolysis and/or acid reduction. For example, a first quantity of the acid may be added while the feed starch/aqueous liquid mixture is at a temperature that is below the gelation temperature (e.g., when the mixture reaches the first temperature and/or up to the onset of gelation). The amount of the first quantity of the acid added may be that suitable to maintain the viscosity of the feed starch/aqueous liquid mixture in a range from about 100 cP to about 8000 cP, preferably from about 300 cP to about 5000 cP. Additionally, or alternatively, the amount of the first quantity of the acid added may be that suitable to maintain the pH of the feed starch/aqueous liquid mixture in a range from about 1 to about 6, preferably from about 3 to about 5.5.

In one embodiment, the degradation agent may include a base. The soluble starch may be degraded by alkali hydrolysis. For example, a first quantity of the base may be added while the feed starch/aqueous liquid mixture is at a temperature that is below the gelation temperature (e.g., when the mixture reaches the first temperature and/or up to the onset of gelation). The amount of the first quantity of the base added may be that suitable to maintain the viscosity of the feed starch/aqueous liquid mixture in a range from about 100 cP to about 8000 cP, preferably from about 300 cP to about 5000 cP. Additionally, or alternatively, the amount of the first quantity of the base added may be that suitable to maintain the pH of the feed starch/aqueous liquid mixture in a range from about 8 to about 14, preferably from about 8.5 to about 10.5.

In one embodiment, the degradation agent may include an oxidizing agent. The soluble starch may be degraded by oxidative reduction. For example, a first quantity of the oxidizing agent may be added while the feed starch/aqueous liquid mixture is at a temperature that is below the gelation temperature (e.g., when the mixture reaches the first temperature and/or up to the onset of gelation). The amount of the first quantity of the oxidizing agent added may be that suitable to maintain the viscosity of the feed starch/aqueous liquid mixture in a range from about 100 cP to about 8000 cP, preferably from about 300 cP to about 5000 cP. Additionally, or alternatively, the amount of the first quantity of the oxidizing agent may range from about 0.0005% to about 30%, preferably from about 0.2% to about 10% based on the weight of dry starch.

In one embodiment, the degradation agent may include a microorganism. The soluble starch may be degraded by microorganism action. For example, a first quantity of the microorganism may be added while the feed starch/aqueous liquid mixture is at a temperature that is below the gelation temperature (e.g., when the mixture reaches the first temperature and/or up to the onset of gelation). The amount of the first quantity of the microorganism added may be that suitable to maintain the viscosity of the feed starch/aqueous liquid mixture in a range from about 100 cP to about 8000 cP, preferably from about 300 cP to about 5000 cP. Additionally, or alternatively, the amount of the first quantity of the microorganism may range from about 0.005% to about 20%, preferably from about 0.2% to about 5% based on the weight of dry starch.

In one embodiment, the degradation agent may include an enzyme. The soluble starch may be enzymatically degraded. For example, a first quantity of the enzyme may be added while the feed starch/aqueous liquid mixture is at a temperature that is below the gelation temperature (e.g., when the mixture reaches the first temperature and/or up to the onset of gelation). The amount of the first quantity of the enzyme added may be that suitable to maintain the viscosity of the feed starch/aqueous liquid mixture in a range from about 100 cP to about 8000 cP, preferably from about 300 cP to about 5000 cP. Additionally, or alternatively, the amount of the first quantity of the enzyme may range from about 0.1 ppm to about 50 ppm, preferably from about 0.3 ppm to about 20 ppm based on the weight of dry starch.

In any of the described embodiments, an increase in the viscosity of the feed starch/aqueous liquid mixture may reduce the flow of the mixture within the vessel or other process equipment and/or through the high shear mixer. This may result in uneven mixing and/or shearing. Additionally, or alternatively, this may result in localized (e.g., in an area surrounding the high shear mixer) heating of the mixture and/or cooking of the feed starch. Subjecting the mixture to the first degradation treatment before the temperature of the feed starch/aqueous liquid mixture reaches the gelation temperature (e.g., prior to the onset of gelation) may decrease the viscosity of the mixture to enable the first mixture to have improved flow characteristics compared to a process without subjecting the mixture to the first degradation treatment. Additionally, or alternatively, reducing the viscosity of the feed starch/aqueous liquid mixture may help to maintain the flow of the mixture within the vessel as the mixture is heated to the gelation temperature, as described herein, to ensure even heating and/or to prevent localized heating within the mixture, which may result in cooking of at least a portion of the feed starch. In other words, subjecting the mixture to the first degradation treatment may enable continued processing of the feed starch/aqueous liquid mixture (e.g., by reducing the viscosity of the mixture) to form the uniform dispersion as described herein. The first degradation treatment may be designed to maintain flow through the high shear mixer without overthinning the mixture. To that end, the first degradation treatment may be designed to degrade the soluble starch present in the feed starch/aqueous liquid mixture by a minimum amount sufficient to maintain flow through the high shear mixer. The amounts provided herein for the various degradation agents are exemplary and may depend on factors such as the solids content of the mixture and/or the type of feed starch being employed.

The first mixture may be heated to a second temperature that is between the gelation temperature and the solubilization temperature. The first mixture may be heated to the second temperature subsequent to subjecting the feed starch/aqueous liquid mixture (e.g., the starch slurry) to the first degradation treatment. The rate of heating (e.g., from the first temperature to the second temperature) may be controlled, which may aid in gelatinizing the feed starch without cooking the feed starch. For example, the rate of heating may be sufficiently slow to enable dissipation of the heat throughout the feed starch/aqueous liquid mixture and/or to avoid localized heating. In one embodiment, the rate of heating may be less than about 0.5° C./min. This rate of heating may be a function of the vessel design (e.g., L/D), the high shear mixer design (e.g., rotor and stator design), the power of the motor driving the high shear mixer, or any other design parameter.

Further heating of the feed starch to the second temperature may cause the feed starch to swell. Additionally, or alternatively, the feed starch may absorb at least a portion of the aqueous liquid. The swelling and/or hydration of the feed starch may enable shearing of the feed starch to form the starch particles of the dispersion. The starch particles may have a size appropriate such that Brownian motion is sufficient to keep them suspended in the dispersion. Although the feed starch may become swollen and/or hydrated, the feed starch may not substantially solubilize in the aqueous liquid (e.g., because the temperature of the feed starch is maintained below the solubilization temperature throughout the process as described herein). Alternatively, the feed starch may substantially solubilize in the aqueous liquid.

The gelation temperature and the solubilization temperature, and thus the first temperature and the second temperature, may depend on the properties of the feed starch. For example, when dent corn starch is used as the feed starch, the gelation temperature may be about 63° C. at atmospheric pressure and/or the solubilization temperature may be about 89° C. at atmospheric pressure. Accordingly, the first temperature may be between about 60° C. and about 66° C. and/or the second temperature may be between about 87° C. and about 91° C. Also for example, when waxy corn starch is used as the feed starch, the gelation temperature may be about 68° C. at atmospheric pressure and/or the solubilization temperature may be about 89° C. at atmospheric pressure. Accordingly, the first temperature may be between about 66° C. and about 70° C. and/or the second temperature may be between about 87° C. and about 91° C.

The gelation temperature and the solubilization temperature may be affected by the pressure at which the process of preparing the dispersion takes place (e.g., the pressure within the vessel). For example, a pressure of from about 101 kPa to about 3447 kPa, about 101 kPa to about 1379 kPa, or about 101 kPa to about 689 kPa may be applied to facilitate processing. Such pressures may be suitable for a continuous process, a semi-continuous process, and/or a batch process.

The feed starch may be sheared to form the starch particles as described herein. The feed starch/aqueous liquid mixture may be maintained at a temperature between the gelation temperature and the solubilization temperature (e.g., the second temperature) during shearing of the feed starch. In this manner, the feed starch may be swollen, as described herein, for shearing.

Upon heating and/or shearing, the viscosity of feed starch/aqueous liquid mixture (e.g., the first mixture) may tend to increase (e.g., due to leaching of low molecular weight starch chains and/or an increase in the amount of soluble starch in the mixture). To aid in controlling the viscosity of the mixture, the soluble starch may be degraded (e.g., reduced or cleaved). The soluble starch may be degraded by subjecting the mixture to a degradation treatment as described herein. For example, the feed starch/aqueous liquid mixture (e.g., the first mixture) may be subjected to a second degradation treatment to form a second mixture. The timing of the second degradation treatment may be critical to producing the desired effects, as described herein. To that end, the mixture may be subjected to the second degradation treatment while the feed starch/aqueous liquid mixture is at a temperature that is between the gelation temperature and the solubilization temperature (e.g., after the onset of gelation). For example, the mixture may be subjected to the second degradation treatment when the mixture reaches the second temperature. In this manner, the feed starch/aqueous liquid mixture may remain and/or be maintained between the gelation temperature and the solubilization temperature while subjected to the second degradation treatment to form the second mixture.

The second degradation treatment may include any suitable degradation treatment as described herein with respect to the first degradation treatment (e.g., addition of a degradation agent, thermal degradation, mechanical degradation, or combinations thereof). The first degradation treatment and the second degradation treatment may be the same as or different than one another. For example, the first degradation treatment and the second degradation treatment may include addition of a degradation agent. Additionally, or alternatively, the first degradation treatment and the second degradation treatment may include thermal degradation and/or mechanical degradation (e.g., thermomechanical degradation). Additionally, or alternatively, one of the first degradation treatment or the second degradation treatment may include addition of a degradation agent, and the other of the first degradation treatment or the second degradation treatment may include thermal degradation and/or mechanical degradation (e.g., thermomechanical degradation). Preferably, the first degradation treatment includes addition of a degradation agent. The first degradation treatment and/or the second degradation treatment may include any suitable combination of the degradation treatments described herein (e,g., addition of a degradation agent and thermal degradation and/or mechanical degradation).

In one embodiment, the second degradation treatment may include addition of a degradation agent as described herein. For example, a second quantity of the degradation agent may be added to the feed starch/aqueous liquid mixture (e.g., the first mixture) to form the second mixture. The second quantity of the degradation agent may be added while the feed starch/aqueous liquid mixture is at a temperature that is between the gelation temperature and he solubilization temperature (e.g., when the first mixture reaches the second temperature and/or after the onset of gelation). In this manner, the feed starch/aqueous liquid mixture may remain and/or be maintained between the gelation temperature and the solubilization temperature during addition of the second quantity of the degradation agent to form the second mixture.

The degradation agent may include any suitable degradation agent as described herein with regard to the first quantity of the degradation agent. The first quantity of the degradation agent and the second quantity of the degradation agent may include the same or different degradation agents Additionally, or alternatively, the first degradation agent and/or the second degradation agent may include any suitable combination of the degradation agents described herein (e.g., an acid, a base, an oxidizing agent, an enzyme, a microorganism, or combinations thereof).

In one embodiment, the degradation agent may include an acid. The soluble starch may be degraded by acid hydrolysis and/or acid reduction. For example, a second quantity of the acid may be added while the feed starch/aqueous liquid mixture is at a temperature that is between the gelation temperature and the solubilization temperature (e.g., when the first mixture reaches the second temperature and/or after the onset of gelation). In one embodiment, the amount of the second quantity of the acid added may be that suitable to maintain the viscosity of the feed starch/aqueous liquid mixture in a range from about 100 cP to about 6000 cP, preferably from about 500 cP to about 4000 cP. Additionally, or alternatively, the amount of the second quantity of the acid added may be that suitable to maintain the pH of the feed starch/aqueous liquid mixture in a range from about 1 to about 6, preferably from about 3 to about 5.5.

In one embodiment, the degradation agent may include a base. The soluble starch may be degraded by alkali hydrolysis. For example, a second quantity of the base may be added while the feed starch/aqueous liquid mixture is at a temperature that is between the gelation temperature and the solubilization temperature (e.g., when the first mixture reaches the second temperature and/or after the onset of gelation). In one embodiment, the amount of the second quantity of the base added may be that suitable to maintain the viscosity of the feed starch/aqueous liquid mixture in a range from about 100 cP to about 6000 cP, preferably from about 500 cP to about 4000 cP. Additionally, or alternatively, the amount of the second quantity of the base added may be that suitable to maintain the pH of the feed starch/aqueous liquid mixture in a range from about 8 to about 14, preferably from about 8.5 to about 10.5.

In one embodiment, the degradation agent may include an oxidizing agent. The soluble starch may be degraded by oxidative reduction. For example, a second quantity of the oxidizing agent may be added while the feed starch/aqueous liquid mixture is at a temperature that is between the gelation temperature and the solubilization temperature (e.g., when the first mixture reaches the second temperature and/or after the onset of gelation). In one embodiment, the amount of the second quantity of the oxidizing agent added may be that suitable to maintain the viscosity of the feed starch/aqueous liquid mixture in a range from about 100 cP to about 6000 cP, preferably from about 500 cP to about 4000 cP. Additionally, or alternatively, the amount of the second quantity of the oxidizing agent may range from about 0.0005% to about 30%, preferably from about 0.2% to about 5% based on the weight of dry starch.

In one embodiment, the degradation agent may include a microorganism. The soluble starch may be degraded by microorganism action. For example, a second quantity of the microorganism may be added while the feed starch/aqueous liquid mixture is at a temperature that is between the gelation temperature and the solubilization temperature (e.g., when the first mixture reaches the second temperature and/or after the onset of gelation). In one embodiment, the amount of the second quantity of the microorganism added may be that suitable to maintain the viscosity of the feed starch/aqueous liquid mixture in a range from about 100 cP to about 6000 cP, preferably from about 500 cP to about 4000 cP. Additionally, or alternatively, the amount of the second quantity of the microorganism may range from about 0.005% to about 20%, preferably from about 0.2% to about 5% based on the weight of dry starch.

In one embodiment, the degradation agent may include an enzyme. The soluble starch may be enzymatically degraded. For example, a second quantity of the enzyme may be added while the feed starch/aqueous liquid mixture is at a temperature that is between the gelation temperature and the solubilization temperature (e.g., when the first mixture reaches the second temperature and/or after the onset of gelation). In one embodiment, the amount of the second quantity of the enzyme added may be that suitable to maintain the viscosity of the feed starch/aqueous liquid mixture in a range from about 100 cP to about 6000 cP, preferably from about 500 cP to about 4000 cP. Additionally, or alternatively, the amount of the second quantity of the enzyme may range from about 0.2ppm to about 40 ppm, preferably from about 0.3 ppm to about 20 ppm based on the weight of dry starch. The enzyme may be deactivated (e.g., after maintaining the viscosity to enable formation of the starch particles of the dispersion). The enzyme may be deactivated using any suitable method such as, for example, heat treatment (e.g., raising or lowering the temperature of the dispersion), adjusting the pH of the dispersion (e.g., to below about 4 or above about 8), addition of a chelating agent to the dispersion, or combinations thereof. Addition of the chelating agent may deactivate the enzyme by co-reacting with calcium ions present in the starch dispersion as a cofactor for the enzyme.

Subjecting the feed starch/aqueous liquid mixture to the second degradation treatment may decrease the viscosity of the mixture to enable the mixture to have improved flow characteristics compared to a process without subjecting the mixture to the second degradation treatment. Additionally, or alternatively, reducing the viscosity of the mixture may help to maintain the flow of the feed starch/aqueous liquid mixture within the vessel as the feed starch is sheared, as described herein, to ensure even heating and/or to prevent localized heating within the mixture, which may result in cooking of at least a portion of the feed starch in the mixture. The second degradation treatment may be designed to maintain stability of the dispersion after 24 hours and/or to degrade the feed starch to a sufficient degree to achieve a desired particle size and/or molecular weight. This may help to ensure utility of the dispersion for a desired application as described herein. The amounts provided herein for the various degradation agents are exemplary and may depend on factors such as the solids content of the mixture and/or the type of feed starch being employed.

In one embodiment, the feed starch may be sheared to form the starch particles of the dispersion. The feed starch may be sheared before the first degradation treatment (e.g., during mixing of the starch slurry), after the first degradation treatment and before the second degradation treatment, and/or after the second degradation treatment. Shearing the feed starch may add heat to the bulk phase of the feed starch/aqueous liquid mixture and/or the starch particles dispersed therein. The residence time of the feed starch, the aqueous liquid, and the starch particles in the mixing zone of the high shear mixer may be kept relatively short (e.g., by maintaining a sufficient flow of the mixture through the high shear mixer). The feed starch may be sheared to form the starch particles in the presence of or in the absence of a cross-linker and/or a surfactant. Controlling the viscosity of the mixture throughout the dispersion process (e.g., with multiple degradation treatments at predetermined times during the process) may aid in maintaining sufficient flow through the high shear mixer. In this manner, localized cooking of the feed starch may be prevented. This is distinguishable from other systems such as, for examples, extruders or jet cookers, which may cause significant localized heating and/or cooking of the feed starch.

In one embodiment, the high shear mixer may be a rotor stator mixer. The rotational speed of the rotor may be adjusted to adjust the amount of shear and/or to form starch particles having the desired particle size. Additionally, or alternatively, the stator may be movable relative to the rotor. For example, the stator may be movable between a 100% position in which there is substantially complete overlap between the rotor and the stator (e.g., the stator is fully engaged with the rotor) and a 0% position in which there is substantially no overlap between the rotor and the stator (e.g., the stator is fully disengaged from the rotor). The stator may be set at any position relative to the rotor between the 100% position and the 0% position (e.g., at a 50% position) such that the stator is partially engaged (e.g., 50% engaged) with the rotor. It will be recognized that the rotor may be movable relative to the stator instead of or in addition to the stator being movable relative to the rotor. The temperature and/or the rate of heating of the feed starch/aqueous liquid mixture (e.g., the starch slurry, the first mixture, the second mixture, and/or the dispersion) may be adjusted by adjusting the position of the stator relative to the rotor. For example, the stator may be at least partially disengaged from the rotor as the temperature of the starch slurry approaches a desired temperature below the gelation temperature (e.g., the first temperature). In this manner, the temperature of the starch slurry may be maintained at a desirable level for the first degradation treatment as described herein. The stator may be at least partially reengaged with the rotor to aid in increasing the temperature of the mixture to between the gelation temperature and the solubilization temperature (e.g., the second temperature). In this manner, the temperature of the mixture may be maintained at a desirable level for the second the degradation treatment and/or shearing of the feed starch into the starch particles as described herein. Additionally, or alternatively, disengaging the stator from the rotor may increase the flow of the mixture through the high shear mixer, and engaging the stator with the rotor may decrease the flow of the mixture through the high shear mixer. Additionally, or alternatively, the high shear mixer may include an auxiliary mixing element (e.g., an agitator). The auxiliary mixing element may be integral with or separate from a primary mixing element (e.g., the rotor stator) of the high shear mixer. The auxiliary mixing element may aid in maintaining flow through the high shear mixer and/or direct the feed starch/aqueous liquid mixture toward and/or away from the mixing zone.

In one embodiment, the starch particles produced as described herein may have an average particle size diameter of about 200 nanometers or less,. The average particle size diameter of the starch particles may be measured using transmission electron microscopy. Measurement of the average particle size diameter of the starch particles using fight scattering techniques may be difficult or even impossible, as the materials appear to loosely agglomerate, giving inaccurate results. In one embodiment, the number-weighted average particle size diameter may be determined by measuring the diameter of a predetermined number of starch particles and then determining the mathematical mean of the diameters of the measured particles to arrive at the number-weighted average particle size diameter.

In one embodiment, the dispersion may have a solids content of at least about 40 wt. % based on a total weight of the dispersion. For example, the dispersion may have a solids content of from about 41 wt. % to about 47 wt. % based on a total weight of the dispersion. Additionally, or alternatively, the dispersion may have a Brookfield viscosity of about 2000 cP or less. The solids content and/or the viscosity of the dispersion may be maintained during storage of the dispersion at ambient conditions for a predetermined period of time. For example, the dispersion having a solids content of at least about 40% may maintain a viscosity of about 2000 cP or less when stored at ambient conditions for 24 hours. After processing, the viscosity of the dispersion may initially increase (e.g., due to cooling). During storage, the prepared dispersion may tend to experience a significant decrease in viscosity with time. This decrease in viscosity may be due to a variety of factors including, for example, starch chain relaxation after shear is removed, reversible agglomeration of particles, and/or the activity of some residual degradation agent remaining in the dispersion. This decrease in viscosity may occur over several days during which the dispersion is left undisturbed.

The multiple degradation treatments may enable the viscosity of the feed starch/aqueous liquid mixture to be controlled for improved processing as described herein. For example, subjecting the mixture to the first degradation treatment at the temperature below the gelation temperature may help to maintain the viscosity of the feed starch/aqueous liquid mixture at a sufficiently low level to enable continued processing of the mixture with the high shear mixer (e.g., to enable sufficient flow through the high shear mixer and/or to prevent localized heating and/or cooking of the feed starch). In the absence of the first degradation treatment, the viscosity of the mixture may become sufficiently high that flow within the high shear mixer is impeded and/or prevented, which may substantially prevent continued heating (e.g., to between the gelation temperature and the solubilization temperature) and/or shearing of the feed starch to form the dispersion as described herein. In other words, the mixture may set up to such an extent that further processing of the mixture becomes difficult or even impossible. This rate and/or extent of the increase in viscosity (e.g., prior to reaching the gelation temperature and/or up to the onset of gelation) may depend on the type of starch used as the feed starch. Subjecting the mixture to the second degradation treatment at the temperature between the gelation temperature and the solubilization temperature may help to maintain the viscosity of the feed starch/aqueous liquid mixture at a sufficiently low level to enable continued processing of the mixture with the high shear mixer (e.g., to enable sufficient flow through the high shear mixer and/or to prevent localized heating and/or cooking of the feed starch). In the absence of the second degradation treatment, the viscosity of the mixture may become sufficiently high that flow within the high shear mixer is impeded and/or prevented, which may substantially prevent shearing of the feed starch to form the dispersion as described herein. In this manner (e.g., by helping to maintain flow of the mixture within the high shear mixer), subjecting the mixture to each of the multiple (e.g., the first and the second) degradation treatments at predetermined points during the process, as described herein, may enable processing of starch slurries having a wide range of solids contents and/or use of a variety of different starches as the feed starch.

The high shear mixer may be any suitable high shear mixer known in the art. For example, the high shear mixer may be a batch high shear mixer, an inline high shear mixer, an ultra high shear inline mixer, or a grinding mill (e.g., a Kady Mill). Additionally, or alternatively, the high shear mixer may be a component of a continuous process, a semi-continuous process, and/or a batch process. Additionally, or alternatively, the high shear mixer may be configured as part of a loop in which material is drawn from a vessel, passed through the high shear mixer, and returned to the vessel.

In one embodiment, the dispersion may be formed using a continuous process. For example, the feed starch and the aqueous liquid may be combined in a stirred tank to form the starch slurry. The starch slurry may be pumped into a first high shear mixer. The starch slurry may pass through the mixer in a single pass. The temperature of the starch slurry may be maintained below the gelation temperature as described herein. The starch slurry may be subjected to the first degradation treatment (e.g., addition of the degradation agent, thermal degradation, and/or mechanical degradation) to form the first mixture. For example, the first quantity of the degradation agent may be added to the mixer through a separate injection port to form the first mixture as described herein. The first mixture may be pumped into a second high shear mixer. The first mixture may pass through the mixer in a single pass. The temperature of the first mixture may be maintained between the gelation temperature and the solubilization temperature as described herein. The feed starch may be sheared (e.g., by the second high shear mixer) as described herein. The first mixture may be subjected to the second degradation treatment to form the second mixture. For example, the second quantity of the degradation agent may be added to the mixer through a separate injection port to form the second mixture as described herein. The second mixture may be pumped to a third high shear mixer to further shear the feed starch to form the starch particles of the dispersion as described herein.

In one embodiment, other conventional additives may be added to the feed starch/aqueous liquid mixture at various points throughout the process (e.g., to the starch slurry, the first mixture, the second mixture, and/or the dispersion). The other additives may include, but are not limited to, an anionic and/or ionic stabilizer (e.g., to reduce particle agglomeration during drying), a plasticizer (e,g., a polyol such as ethylene glycol, propylene glycol, polyglycols, glycerol, sucrose, maltose, maltodextrins, and sugar alcohols (e.g., sorbitol), urea, sodium lactate, amino acids, or citric acid esters), a lubricant (e.g., lecithin, other phospholipids, or monoglycerides), a biocide, an anti-microbial additive, a base and/or an acid (e.g., for pH adjustment), a pigment, a flavor and/or fragrance enhancer, an inorganic and/or organic inert filler and/or pigments, or combinations thereof.

In one embodiment, the dispersion may be used without any additional processing (e.g., drying and/or concentration). Alternatively, at least a portion of the aqueous liquid may be removed from the dispersion to increase the concentration of the starch particles (e.g., the solids content of the dispersion) and/or to form a dry redispersible powder of the starch particles, which may be redispersed in a subsequent process. Any suitable process known in the art may be used to remove at least a portion of the aqueous liquid from the dispersion including, for example, air drying, forced air drying, spray drying, pressurized filtration, and centrifugation. The dry powders may be blended with other powders, compounds, and/or dispersions such as, for example, latexes, latex and non-latex binders, dispersions, and/or pigments, which may be used for film coating, adhesive, and/or binder systems.

In one embodiment, the dispersion may be blended, to produce a coating color or other mixture, with one or more additional components such as, for example, a filler; an additive; a pigment (e.g., titanium dioxide, mica, calcium carbonate, silica, zinc oxide, milled glass, aluminum trihydrate, talc, antimony trioxide, fly ash, and clay); a co-solvent (e.g., glycols, glycol ether, 2,2,4-trimethyl-1,3-pentanediol monoisobutyrate, alcohols, mineral spirits, and benzoate esters); a binder composition (e.g., acrylic latex, vinyl acrylic latex, styrene acrylic latex, styrene butadiene latex, vinyl acetate ethylene latex, modified cellulosic binders such as methylcellulose, hydroxypropyl cellulose, and combinations thereof); a dispersant (e.g., aminoalcohols, and polycarboxylates); a surfactant; a defoamer (e.g., any compound that reduces and/or binders the formation of foam in a liquid); a preservative (e.g., biocides, mildewcides, fungicides, algaecides, and combinations thereof); a thickener (e.g., cellulosic based thickeners such as hydroxyethyl cellulose, hydrophobically modified alkali soluble emulsions (HASE) thickeners such as UCAR® POLYPHOBE TR-116 from The Dow Chemical Company and hydrophobically modified ethoxylated urethane thickeners (HEUR)); a neutralizing agent (e.g., hydroxides, amines, ammonia, and/or carbonates); and/or a polysaccharide derivative (e.g., cellulose derivatives such as polysaccharide ethers and esters, cellulose ethers and esters, and water-soluble cellulose ethers). The additional component may include one or more of the following substituents: hydroxyethyl, hydroxypropyl, hydroxybutyl, methyl, ethyl, propyl, dihydroxypropyl carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate, or sulfate, of which some groups, such as, for example, hydroxyethyl, hydroxypropyl, hydroxybutyl, dihydroxypropyl and lactate, are capable of forming grafts. Typical polysaccharide derivatives include, for example, guar derivatives, starch derivatives, chitin or chitosan derivatives, and cellulose derivatives.

Examples of cellulose derivatives may include, for example, hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methyl cellulose (MC), methyl hydroxypropyl cellulose (MRPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CMSEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) hydrophobically modified hydroxyethyl hydroxypropyl sulfoethyl cellulose (hmHEHPSEC). Other suitable cellulose derivatives may include cellulose ethers having a thermal flocculation point in water, such as, for example, methyl cellulose, methyl hydroxyethyl cellulose, methyl hydroxypropyl cellulose and hydroxypropyl cellulose.

Examples of colorants may include dyes, pigments, predispersions, fluorescent whitening agents, and optical brighteners. The colorants may be used singly, in a mixture, or as a solid solution. Pigments may be provided, for example, in the form of raw pigments, treated pigments, pre-milled pigments, pigment powders, pigment presscakes, pigment masterbatches, recycled pigment, and solid or liquid pigment predispersions. As used herein, a raw pigment is a pigment particle that has had no wet treatments applied to its surface, such as to deposit various coatings on the surface. Raw pigment and treated pigment are further discussed in PCT Publication No. WO 2005/095277 and U.S. Patent Application Publication No. 2006/0078485, the relevant portions of which are incorporated herein by reference. In contrast, a treated pigment may have undergone wet treatment, such as to provide metal oxide coatings on the particle surfaces. Examples of metal oxide coatings include alumina, silica, and zirconia. Recycled pigment may be used as the starting pigment particles, where recycled pigment is pigment after wet treatment of insufficient quality to be sold as coated pigment.

Exemplary colorant particles may include, for example, pigments such as yellow coloring agent, compounds typified by a condensed azo compound, an isoindolynone compound, an anthraquinone compound, an azometal complex methine compound, and an allylamide compound as pigments may be used. As a magenta coloring agent, a condensed azo compound, a diketopyrrolopyrrole compound, anthraquinone, a quinacridone compound, a base dye lake compound, a naphthol compound, a benzimidazolone compound, a thioindigo compound, and a perylene compound. As a cyan coloring agent, a copper phthalocyanine compound and its derivative, an anthraquinone compound, a base dye lake compound, and the like may be used.

The dispersion may be used as a coating composition. The dispersion may be used, for example, in coating applications (e.g., architectural coating applications, automotive coating applications, paper coating applications, paper sizing applications, seed coating applications, conductive coatings, pharmaceutical coating applications, and/or industrial coating applications), adhesives applications (e.g., tapes, labels, book bindings, corrugations, etc.), binder applications (e.g., in wet laminations and/or wood composites, fiberglass shingle mats, and/or polyester spun-bond applications such as roofing and carpet backing), sealant applications, foam applications, toner applications, immediate release coating applications, and controlled released coating applications. Additionally, or alternatively, the dispersion may be used in any conventional application in which starch and/or latex are used. For example, the dispersion can be used in a paper coating composition in which a conventional binder (e.g., latex) and/or a conventional coating starch may be partially or wholly replaced with the dispersion.

Suitable substrates for the coating applications may include, for example, cellulosic based materials (e.g., paper, paper board, and/or cardboard), metal based materials, polymeric based materials (e.g., synthetic and/or natural polymeric materials), and/or mineral based materials (e.g., concrete). The dispersions may be used in any conventional starch application, synthetic latex application, coating application, and/or latex formulation, in which the latex may be partially or wholly replaced by the dispersion.

EXAMPLES

The following examples are given to illustrate embodiments of the present disclosure and should not be construed as limiting its scope. All parts and percentages are by weight unless otherwise indicated.

Test Methods

Brookfield Viscosity

The viscosity is measured using a Brookfield RVT viscometer (available from Brookfield Engineering Laboratories, Inc., Stoughton, Mass., USA). For viscosity determination, a sample is poured into a suitably large container to avoid edge effects between the wall and the spindle. The viscosity is measured at around 25° C. with a variety of spindle sizes and rotation speeds depending on the characteristics of the sample being measured. The values reported in Table 1 were obtained with a number 4 spindle and 100-rpm condition.

Solids

Solids content is measured using a CEM Smart System 5 microwave or equivalent. Typically it is required to run at a low power setting to avoid burning of the starch material upon heating.

Stability

Dispersion stability is determined using a combination of low shear viscosity and a visual observation of the starch dispersion. A dispersion that forms a gel typically will not provide a measurement via the Brookfield rheometer. A stable dispersion will allow a measurement via the Brookfield rheometer.

Materials

The following materials are used in the examples.

Waxy Starch: waxy corn starch (Waxy Corn Starch available from Tate & Lyle, Lafayette, Ind., USA), dry powder containing about 11% moisture.

Dent Starch: dent corn starch (Pearl Starch available from Penford, Cedar Rapids, Iowa, USA or Tate & Lyle, Lafayette, Ind., USA), dry powder containing about 11% moisture.

Ammonium Persulfate: 98% ammonium persulfate solution (Acros Organics, N.J., USA), diluted to a 40% solution with distilled water, Sodium Hypochlorite: 12.5% sodium hydrochloride with 87.5% inert ingredients (TECH GROUP SWIMMING POOL SANITIZER PLUS, distributed by Cul-Mac Industries, Inc., Wayne, Mich., USA).

Enzyme: enzyme preparation (BAN 480L available from Novozymes A/S Bagsvaerd, Denmark). For the examples using the Kady Mill, the enzyme is diluted to a 10% solution with distilled water.

Caustic: 20% sodium hydroxide solution (Fisher Scientific, Fair Lawn, N.J., USA).

Hydrochloric Acid: 0.1 N hydrochloric add solution (RICCA Chemical Company, Arlington, Tex., USA).

Calcium Chloride: 10 weight percent solution of calcium chloride in water (Calcium chloride from Fischer Scientific, Fair Lawn, N.J., USA).

Water: De-Ionized Water.

Equipment

Rotor Stator Mixer: rotor stator mixer (model RW 60 S-VST Rotor Stator available from GAW Pidlner-Steinburg GmbH, Graz, Austria) with 50 hp motor drive and a 473 liter container.

Kady Mill: Lab Kady-Mill mixer (model L-744 available from Kady International, Scarborough, Me., USA) with Stator #1 mixing head, 7.5 hp motor drive, and a 1 gallon stainless steel water jacketed vessel for heating or cooling.

Example 1

At room temperature (~25° C.), 1924 g of waxy starch and 2356 g of water are combined to form a mixture having a 43 weight percent solids content and then pre-slurried with a standard laboratory mixing device. The mixture is transferred to the vessel of the Kady Mill. The mixture having the 43 weight percent solids content is mixed under shear for 18 minutes. After the 18 minutes of mixing, 77.4 g of ammonium persulfate solution is added to the vessel. The temperature in the vessel at the time of the first ammonium persulfate addition is 145.8° F. (63.2° C.), which is below the gelation temperature of the waxy starch. Mixing is continued for 5 minutes. After the 5 minutes of mixing, an additional 154.8 g of ammonium persulfate solution is added to the vessel. The temperature in the vessel at the time of the second ammonium persulfate addition is 161.4° C. (71.9° C.), which is between the gelation temperature and the solubilization temperature of the waxy starch. Mixing is continued for 16 minutes. After the 16 minutes of mixing, an additional 154.8 g of ammonium persulfate solution is added to the vessel. Mixing is continued for 5 minutes. After the 5 minutes of mixing, an additional 154.8 g of ammonium persulfate solution is added to the vessel. Mixing is continued for 34 minutes. Cooling water supply is activated, and mixing is continued for 5 minutes. During the 5 minutes of mixing, the temperature in the vessel is reduced to 104.7° F. (40.4° C.) using the cooling jacket. The pH is adjusted to 8.8 by addition of 671.4 g of caustic. A preservative is added to the vessel.

The result is a stable dispersion of starch particles in the aqueous liquid that does not gel after storage at room temperature (~25° C.) for 24 hours. The solids content of the stable starch dispersion is 41.9% with an initial viscosity of 42 cP. After 24 hours, the viscosity of the starch dispersion is 54 cP.

Example 2

At room temperature (~25° C.), 1924 g of waxy starch and 2356 g of water are combined to form a mixture having a 43 weight percent solids content and then pre-slurried with a standard laboratory mixing device. The mixture is transferred to the vessel of the Kady Mill. The mixture having the 43 weight percent solids content is mixed under shear for 21 minutes. After the 21 minutes of mixing, 306.73 g of sodium hypochlorite is added to the vessel. The temperature in the vessel at the time of the sodium hypochlorite addition is 145 (62.8° C.), which is below the gelation temperature of the waxy starch. Mixing is continued for 46 minutes. During the 46 minutes of mixing, the pH is adjusted to 6 by addition of about 10 g of caustic. After the 46 minutes of mixing, 4.6 g of enzyme is added to the vessel. The temperature in the vessel at the time of the enzyme addition is 170.1° F. (76.7° C.), which is between the gelation temperature and the solubilization temperature of the waxy starch. Mixing is continued for 60 minutes. During the 60 minutes of mixing, the temperature in the vessel is maintained between 170.1° F. (76.7° C.) and 189.6° F. (87.6° C.), which is between the gelation temperature and the solubilization temperature of the waxy starch. Mixing is continued for 7 minutes. During the 7 minutes of mixing, the temperature in the vessel is reduced to 110.5° F. (43.6° C.) using the cooling jacket. During the 7 minutes of mixing, a preservative is added to the vessel.

The result is a stable dispersion of starch particles in the aqueous liquid. The solids content of the stable starch dispersion is 44% with an initial viscosity of 402 cP at 101° F. (38.3° C.)

Example 3

An amount of waxy starch and an amount of water, both at room temperature (~25° C.), are measured to make a mixture having a 44 weight percent solids content, 200 lb of waxy starch and 235 lb of water are combined in the tank of the rotor stator mixer. 44 g of caustic and 50.5 g of calcium chloride are added to the tank. The speed setting of the mixer is set to 1800 rpm on the motor drive speed control, and the mixture having the 44 weight percent solids content is mixed under shear for 63 minutes. After the 63 minutes of mixing, 8.7 g of enzyme is added to the tank. The mixing zone temperature at the time of the first enzyme addition is 145° F. (62.8° C.), which is below the gelation temperature of the waxy starch. The bulk temperature is 145° F. (62.8° C.). Mixing is continued for 143 minutes. After the 143 minutes of mixing, an additional 8.7 g of enzyme is added to the tank. The mixing zone temperature at the time of the second enzyme addition is 180° F. (82.2° C.), which is between the gelation temperature and the solubilization temperature of the waxy starch. The bulk temperature is 180° F. (82.2° C.). Mixing is continued for 45 minutes. During the 45 minutes of mixing, the mixing zone temperature is maintained between 179° F. (81.7° C.) and 184° F. (84.4° C.), which is between the gelation temperature and the solubilization temperature of the waxy starch. The speed setting of the mixer is reduced to 900 rpm on the motor drive speed control, and mixing is continued for 59 minutes. During the 59 minutes of mixing, the mixing zone temperature is reduced to 120° F. (48.9° C.). The bulk temperature is reduced to 120° F. (48.9° C.). The enzyme is deactivated, and a preservative is added to the tank.

The result is a stable dispersion of starch particles in the aqueous liquid that does not gel after storage at room temperature (~25° C.) for 24 hours. The solids content of the stable starch dispersion is 45% with an initial viscosity of 92 cP at 112° F. (44.4° C.). After 4 days, the starch dispersion remains stable with a viscosity of 118 cP.

Example 4

At room temperature (~25° C.), 1924 g of dent starch and 2356 g of water are combined to form a mixture having a 41 weight percent solids content and then pre-slurried with a standard laboratory mixing device. The mixture is transferred to the vessel of the Kady Mill. The mixture having the 41 weight percent solids content is mixed under shear for 36 minutes. After the 36 minutes of mixing, 394.83 g of ammonium persulfate is added to the vessel. The temperature in the vessel at the time of the first ammonium persulfate addition is 145° F. (62.8° C.), which is below the gelation temperature of the dent starch. Mixing is continued for 14 minutes. After the 14 minutes of mixing, an additional 219.35 g of ammonium persulfate is added to the vessel. The temperature in the vessel at the time of the second ammonium persulfate addition is 176.2° F. (80.1° C.), which is between the gelation temperature and the solubilization temperature of the dent starch. Mixing is continued for 131 minutes. During the 131 minutes of mixing, the Kady Mill is stopped periodically, and the mixture is stirred by hand. During the 131 minutes of mixing, the temperature in the vessel is maintained between 177.1° F. (80.6° C.) and 189.6° F. (87.6° C.), which is between the gelation temperature and the solubilization temperature of the dent starch. Mixing is continued for 6 minutes. During the 6 minutes of mixing, the temperature in the vessel is reduced to 120° F. (48.9° C.) using the cooling jacket. The pH is adjusted to 5.5 by addition of 459.69 g of caustic. A preservative is added to the vessel.

The result is a stable dispersion of starch particles in the aqueous liquid. The solids content of the stable starch dispersion is 42.5% with an initial viscosity of 484 cP at 103° F. (39.4° C.).

Example 5

An amount of dent starch and an amount of water, both at room temperature (~25° C.), are measured to make a mixture having a 42 weight percent solids content. 250 lb of dent starch and 328 lb of water are combined in the tank of the rotor stator mixer. 5 g of caustic and 63.1 g of calcium chloride are added to the tank. The speed setting of the mixer is set to 1800 rpm on the motor drive speed control, and the mixture having the 42 weight percent solids content is mixed under shear for 100 minutes. After the 100 minutes of mixing, 9.1 g of enzyme is added to the tank. The mixing zone temperature at the time of the first enzyme addition is 142° F. (61.1° C.), which is below the gelation temperature of the dent starch. The bulk temperature is 129° F. (53.9° C.). Mixing is continued for 36 minutes. After the 36 minutes of mixing, an additional 30.3 g of enzyme is added to the tank. The mixing zone temperature at the time of the second enzyme addition is 191° F. (88.3° C.), which is between the gelation temperature and the solubilization temperature of the dent starch. The bulk temperature is 131° F. (55° C.). Mixing is continued for 63 minutes. During the 63 minutes of mixing, the mixing zone temperature is maintained between 163° F. (72.8° C.) and 191° F. (88.3° C.), which is between the gelation temperature and the solubilization temperature of the dent starch. During the 63 minutes of mixing, the enzyme is deactivated. The speed setting of the mixer is reduced to 900 rpm on the motor drive speed control, and mixing is continued for 109 minutes. During the 109 minutes of mixing, the mixing zone temperature is reduced to 106° F. (41.1° C.). The bulk temperature is reduced to 104° F. (40° C.). A preservative is added to the tank.

The result is a stable dispersion of starch particles in the aqueous liquid that does not gel after storage at room temperature (~25° C.) for 24 hours. The solids content of the stable starch dispersion is 41.5% with an initial viscosity of 800 cP at 104° F. (40° C.). After 24 hours, the viscosity of the starch dispersion is 662 cP. After 4 days, the starch dispersion remains stable with a viscosity of 600 cP. After 5 days, the starch dispersion remains stable with a viscosity of 600 cP.

Comparative Example A

An amount of dent starch and an amount of water, both at room temperature (~25° C.), are measured to make a mixture having a 41 weight percent solids content. 250 kg of dent starch and 297 kg of water are combined in the tank of the rotor stator mixer. 210 g of caustic and 63 g of calcium chloride are added to the tank. The speed setting of the mixer is set to 1800 rpm on the motor drive speed control, and the mixture having the 41 weight percent solids content is mixed under shear for 99 minutes. After the 99 minutes of mixing, 9.1 g of enzyme is added to the tank. The mixing zone temperature at the time of the enzyme addition is 176° F. (80° C.), which is between the gelation temperature and the solubilization temperature of the dent starch. The bulk temperature is 156° F. (68.9° C.). Mixing is continued for 2 minutes. After the 2 minutes of mixing, the material in the tank sets up such that there is substantially no flow in the bulk area of the mixer. Substantial overheating is observed around the rotor stator, and the material is unstable (i.e., the material is irreversibly gelled).

Comparative Example A illustrates the effect of employing the first degradation treatment at a temperature below the gelation temperature and the second degradation treatment at a temperature between the gelation temperature and the solubilization temperature. Flow is maintained through the mixing zone of the mixer in Examples 4-5 even though the feed starch is dent starch and the feed starch/aqueous liquid mixture has a high solids content (e.g., at least 40%) throughout the process. For example, the dispersion is not diluted to a lower solids content (e.g., 25%) for storage. It is believed that multiple degradation treatments at the predetermined times during the process, as described herein, effectively control the viscosity of the feed starch/aqueous liquid mixture to enable completion of the shearing process during the gelation phase while maintaining the high solids content.

TABLE 1

Brookfield Viscosity Values for the Dispersions of Examples 1-5 and Comparative Example A

| Example | Target Weight Percent Solids Content During Shear | Weight Percent Solids Content During Storage | Brookfield Viscosity [cP] | | |
|---|---|---|---|---|---|
| | | | Initial | 1 day | 4 day |
| Example 1 | 43 | 41.9 | 42 | 54 | |
| Example 2 | 43 | 44 | 402 | | |
| Example 3 | 44 | 45 | 92 | | 118 |
| Example 4 | 41 | 42.5 | 484 | | |
| Example 5 | 42 | 41.5 | 800 | 662 | 600 |
| Comparative Example A | 41 | nm | nm | nm | nm | nm = not measurable - sample gelled

What is claimed is:

1. A process for preparing a starch dispersion comprising:
   combining a feed starch and an aqueous liquid to form a starch slurry;
   subjecting the starch slurry to a first degradation treatment to form a first mixture, wherein a temperature of the starch slurry during the first degradation treatment is less than a gelation temperature;
   heating the first mixture to a temperature between the gelation temperature and a solubilization temperature;
   subjecting the heated first mixture to a second degradation treatment to form a second mixture; and
   shearing the second mixture to form the starch dispersion.

2. The process of claim 1, wherein each of subjecting the starch slurry to the first degradation treatment and subjecting the heated first mixture to the second degradation treatment comprises reducing a molecular weight of soluble starch from a first molecular weight to a second molecular weight that is less than the first molecular weight.

3. The process of claim 1, wherein the first degradation treatment and the second degradation treatment are independently selected from the group consisting of addition of a degradation agent, thermal degradation, mechanical degradation, and combinations thereof.

4. The process of claim 1, wherein at least one of subjecting the starch slurry to the first degradation treatment or subjecting the heated first mixture to the second degradation treatment comprises adding a degradation agent to the respective starch slurry or heated first mixture.

5. The process of claim 1, wherein subjecting the starch slurry to the first degradation treatment comprises adding a first quantity of a degradation agent to the starch slurry and subjecting the heated first mixture to the second degradation treatment comprises adding a second quantity of the degradation agent to the heated first mixture.

6. The process of claim 5, wherein the degradation agent is selected from the group consisting of an acid, a base, an oxidizing agent, an enzyme, a microorganism, and combinations thereof.

7. The process of claim 1, further comprising maintaining the temperature of the second mixture during shearing between the gelation temperature and the solubilization temperature.

8. The process of claim 1, further comprising combining the feed starch and the aqueous liquid with a high shear mixer.

9. The process of claim 1, wherein heating the first mixture comprises processing the first mixture with a high shear mixer.

10. The process of claim 1, wherein heating the first mixture comprises increasing the temperature of the first mixture by no more than 0.5° C./min from a first temperature that is below the gelation temperature to a second temperature that is between the gelation temperature and the solubilization temperature.

* * * * *